(12) United States Patent
To

(10) Patent No.: US 9,047,272 B1
(45) Date of Patent: *Jun. 2, 2015

(54) SYSTEM AND METHODS FOR INDEX SELECTION IN COLLECTIONS OF DATA

(71) Applicant: Quest Software, Inc., Aliso Viejo, CA (US)

(72) Inventor: Wai-Yip To, Hong Kong (CN)

(73) Assignee: Dell Software Inc., Aliso Viejo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/934,912

(22) Filed: Jul. 3, 2013

Related U.S. Application Data

(63) Continuation of application No. 12/939,637, filed on Nov. 4, 2010, now Pat. No. 8,499,001.

(60) Provisional application No. 61/264,437, filed on Nov. 25, 2009.

(51) Int. Cl.
*G06F 17/30* (2006.01)
*G06F 19/28* (2011.01)

(52) U.S. Cl.
CPC ...................................... *G06F 19/28* (2013.01)

(58) Field of Classification Search
CPC  G06F 17/3064; G06F 17/30864; G06F 19/28
USPC ......... 707/741, 758, 766, 767, 771, 802, 803, 707/999.002, 41
See application file for complete search history.

(56) References Cited

U.S. PATENT DOCUMENTS

| | | | |
|---|---|---|---|
| 5,960,423 A | 9/1999 | Chaudhuri et al. | |
| 6,513,029 B1 | 1/2003 | Agrawal et al. | |
| 6,934,701 B1 | 8/2005 | Hall, Jr. | |
| 8,499,001 B1 * | 7/2013 | To ................................. | 707/767 |

(Continued)

OTHER PUBLICATIONS

Kovacevic, V. et al., "A Genetic Algorithm Based Tool for the Database Index Selection Problem," Oct. 2005, available from http://www.hermes-softlab.com/news/rel/att/IS2005KovacevicFilipic.pdf, in 4 pages.

(Continued)

*Primary Examiner* — Greta Robinson
(74) *Attorney, Agent, or Firm* — Winstead PC

(57) ABSTRACT

Systems and methods are disclosed that utilize a genetic algorithm to search for an index configuration for a collection of data such as, e.g., a database. Genetic algorithms can include stochastic search heuristics that mimic processes of natural evolution including inheritance, mutation, crossover, and selection. A population of chromosomes representing candidate index configurations can evolve to increase or optimize the fitness of the population and to identify the best (e.g., most fit) index configuration. Fitness of a chromosome may be measured based at least in part on the cost of computer resources used for executing Structured Query Language (SQL) statements in the indexed database. In various implementations, virtual indexing may be used to simulate building an index, chromosomes may be encoded using non-bit-mapped representations of index configurations, chromosomes may include genes representing a column in a table in a database, dropping an index from a table in a database, or a composite index for a database, and/or a participation pool may be used to select fitter genes for an initial population of chromosomes.

19 Claims, 6 Drawing Sheets

(56) References Cited

U.S. PATENT DOCUMENTS

| | | | |
|---|---|---|---|
| 2003/0093408 A1* | 5/2003 | Brown et al. | 707/2 |
| 2003/0204588 A1* | 10/2003 | Peebles et al. | 709/224 |
| 2007/0208691 A1 | 9/2007 | Ramakrishnan | |
| 2010/0057796 A1* | 3/2010 | Brown et al. | 707/715 |

OTHER PUBLICATIONS

Kovacevic, V. et al., "A Genetic Algorithm with an Adaptation Mechanism for Database Index Optimization," in 2nd International Conference on Bioinspired Optimization Methods and their Applications, eds. B. Filipic, et al., Oct. 2006, pp. 111-120.

Kratica, J., et al., "A Genetic Algorithm for the Index Selection Problem," Lecture Notes in Computer Science, Proceedings of the 2003 International Conference on Applications of Evolutionary Computing, Apr. 2003, in 11 pages.

Negnevitsky, M., "Evolutionary Computation," Chapter 7 in "Artificial Intelligence, A Guide to Intelligent Systems," Addison-Wesley, 2nd edition, 2005, pp. 219-257.

\* cited by examiner

SYSTEM AND METHODS FOR INDEX SELECTION IN COLLECTIONS OF DATA

CROSS-REFERENCE TO RELATED APPLICATIONS

This application is a continuation of U.S. patent application Ser. No. 12/939,637, filed on Nov. 4, 2010. U.S. patent application Ser. No. 12/939,637 claims the benefit of priority under 35 U.S.C. §119(e) of U.S. Provisional Patent Application No. 61/264,437, filed on Nov. 25, 2009. U.S. patent application Ser. No. 12/939,637 and U.S. Provisional Patent Application No. 61/264,437 are hereby incorporated by reference herein in their entirety to be considered part of this specification.

BACKGROUND

1. Field

Embodiments of the disclosure generally relate to systems and methods for organizing a collection of data stored in a computer system, and more particularly to managing and improving database and resource performance.

2. Description of the Related Art

Collections of data can be stored in a variety of ways on a computer system. For example, the collection of data may be stored as a database such as, e.g., a relational database. An advantage of a relational database is the ability to extract data from the database using intuitive Structured Query Language (SQL) statements. Business professionals and data analysts can therefore access a relational database without having specialized programming skills.

A database management system (DBMS) may provide one or more indexes that can improve the speed or efficiency of data access or retrieval operations from the database. An index can be organized as a data structure such as, e.g., a tree, a hash, a bitmap, a linked list, and so forth. For example, an index for a relational database may be a data structure (e.g., a B-tree) that organizes one or more columns of a database table in a specific order and provides pointers to database values stored in specific columns or combinations of columns in a table.

The problem of finding an efficient or optimal index configuration (e.g., a set of indexes) for a target database is computationally challenging. For example, a database may have hundreds or thousands of tables and there may be thousands (or more) SQL statements for the database. The number of possible index configurations for such a database can be enormous, and searching for an index configuration that provides desired benefits (e.g., in terms of database performance, resource usage, etc.) can be time and resource intensive.

SUMMARY

In view of the foregoing and other challenges, certain embodiments of the systems and methods described herein utilize a genetic algorithm (GA) to efficiently search for index configurations for a target database. Genetic algorithms include stochastic search heuristics that mimic processes of natural evolution including inheritance, mutation, crossover, and selection. In some implementations, candidate index configurations for the target database "evolve" in order to increase or optimize the "fitness" of a population of "chromosomes" that represent possible index configurations. The fitness of a chromosome may be measured, for example, based at least in part on the cost of computer resources used for executing SQL statements in the indexed database. Embodiments of the systems and methods may use virtual indexing to simulate building an index, which may improve performance since the index is not actually built in the database. Some embodiments of the genetic algorithm use gene crossover and/or mutation to evolve the population of chromosomes to form a new generation of offspring with increased fitness. Evolution can continue until a termination criterion (or criteria) is met, for example, a maximum number of generations (e.g., 100 generations), a maximum computer processing time, and/or a satisfactory level of fitness is found.

As will be further described herein, in some embodiments, the length of the chromosome and/or the number of chromosomes can be allowed to increase (or decrease) during the evolution. In some embodiments, chromosomes for candidate indexes can be encoded using a conventional bitmap of binary digits (which may use thousands of bits to represent an index configuration). In other embodiments, chromosomes can be advantageously encoded using a non-bitmapped representation of the index configuration, which may in some cases improve performance compared to a bitmapped chromosomal representation. Chromosomes may include genes to represent one or more of the following: a column in a table in the database, dropping an index from a table in the database, and/or a composite index for the database. In some embodiments, a participation pool is used to select better genes for the initial population of chromosomes, which may reduce the time for finding an improved or optimal solution. In some embodiments, a probabilistic method is used for determining the length of a potential composite index. Some implementations of the disclosed systems and methods use one, some, or all of the following: (i) growing chromosomes in length and/or in number during the evolution, (ii) non-bitmapped encodings for chromosomes, (iii) a participation pool for the genes, and (iv) a probabilistic method for constructing a composite index.

In one aspect of the disclosure, a system for managing index configurations for a database is described. The system includes an index selection subsystem that can be configured to communicate with a data repository, which can be configured to store a database. The index selection subsystem can be configured to execute one or more modules on a computing device. The index selection subsystem may include one or more of: a population module, a fitness module, an evolution module, and an interface module. The population module can be configured to provide a population of chromosomes that represent possible index configurations for the database. In some implementations, a chromosome includes at least one gene associated with a possible index candidate for the database. The fitness module can be configured to provide a fitness for each of the chromosomes in the population. The evolution module can be configured to evolve the population of chromosomes based at least in part on one or more genetic operators. The evolution module can be further configured to (1) increase the number of chromosomes in the population in response to a first criterion or (2) increase the length of at least some of the chromosomes in the population in response to a second criterion, or both (1) and (2). The interface module can be configured to provide information associated with one or more of the chromosomes in the population.

In another aspect of the disclosure, a method for finding an index configuration for a database is described. The method may be performed under control of a computing system that includes one or more physical computing devices. The method may include determining, from a plurality of structured query language (SQL) statements for a database, a set of index candidates for the database. The index candidates can include at least one of: (1) a column in a table in the database, (2) dropping an index associated with a table in the database, and (3) a composite index for the database, with the composite index including a plurality of columns from at least one table in the database. The method can further include forming a gene pool that includes a plurality of genes associated with the index candidates for the database. Each gene may include a representation of an index candidate from the set of index candidates. In some implementations, the representation includes an alphanumeric identifier for the index candidate. The method may further include determining a participation probability for each gene in the gene pool. The participation probability for a gene can be based at least in part on a total cost of the plurality of SQL statements for the index candidate associated with the gene. The method may also include generating a parent population of chromosomes. Each chromosome can include one or more genes from the gene pool. Generating the parent population of chromosomes may include filling a gene in a chromosome based at least in part on the participation probability for that gene. The method may further include evolving the parent population of chromosomes to form an offspring population of chromosomes. Evolving the parent population of chromosomes may include applying at least one of a crossover operator and a mutation operator to at least some of the chromosomes in the parent population. The method may also include determining a fitness of each of the chromosomes in the offspring population, evaluating whether to terminate the evolving based at least in part on a termination criterion, and providing information associated with one or more of the chromosomes in the offspring population.

In another aspect, a method for recommending an index configuration for a collection of data is described. The method can include analyzing a plurality of transactions for a collection of data to determine a set of index candidates for the collection of data. The method can also include generating a group of index configurations for the collection of data. Each index configuration may be associated with a plurality of index candidates from the set of index candidates, and the index candidates may be represented in the index configuration as a non-bitmapped data structure in some implementations. The method can also include evaluating a fitness of each index configuration in the group of index configurations. The fitness can be based at least in part on a change in the anticipated computer resources associated with using the index configuration when executing the plurality of transactions on the collection of data. The method further can include changing, for each index configuration in the group of index configurations, a first index candidate of the plurality of index candidates in the index configuration. Changing the first index candidate can include (1) mutating the first index candidate to a second index candidate selected from the set of index candidates based at least in part on a mutation probability, with the second index candidate being different from the first index candidate; (2) replacing the first index candidate with a second index candidate selected from a second index configuration from the group of index configurations, with the second index configuration selected based at least in part on a recombination probability; or both (1) and (2). The recombination probability can be based at least in part on the fitness associated with the second index configuration. The method can also include modifying the group of index configurations by (1A) adding new index configurations to the group of index configurations, with the new index configurations including index candidates selected from the set of index candidates; (2A) adding new index candidates from the set of index candidates to each of the index configurations present in the group of index configurations, or both (1A) and (2A). In some implementations, the method includes repeating, one or more times, evaluating the fitness, changing the first index candidate, and modifying the group of index configurations. The method can also include recommending, from the group of index configurations, the index configuration having the greatest fitness (e.g., the greatest fitness found to that point during performance of the method). In some implementations, some or all of the method may be performed by a computing system that includes one or more physical computing devices.

Figure 1:
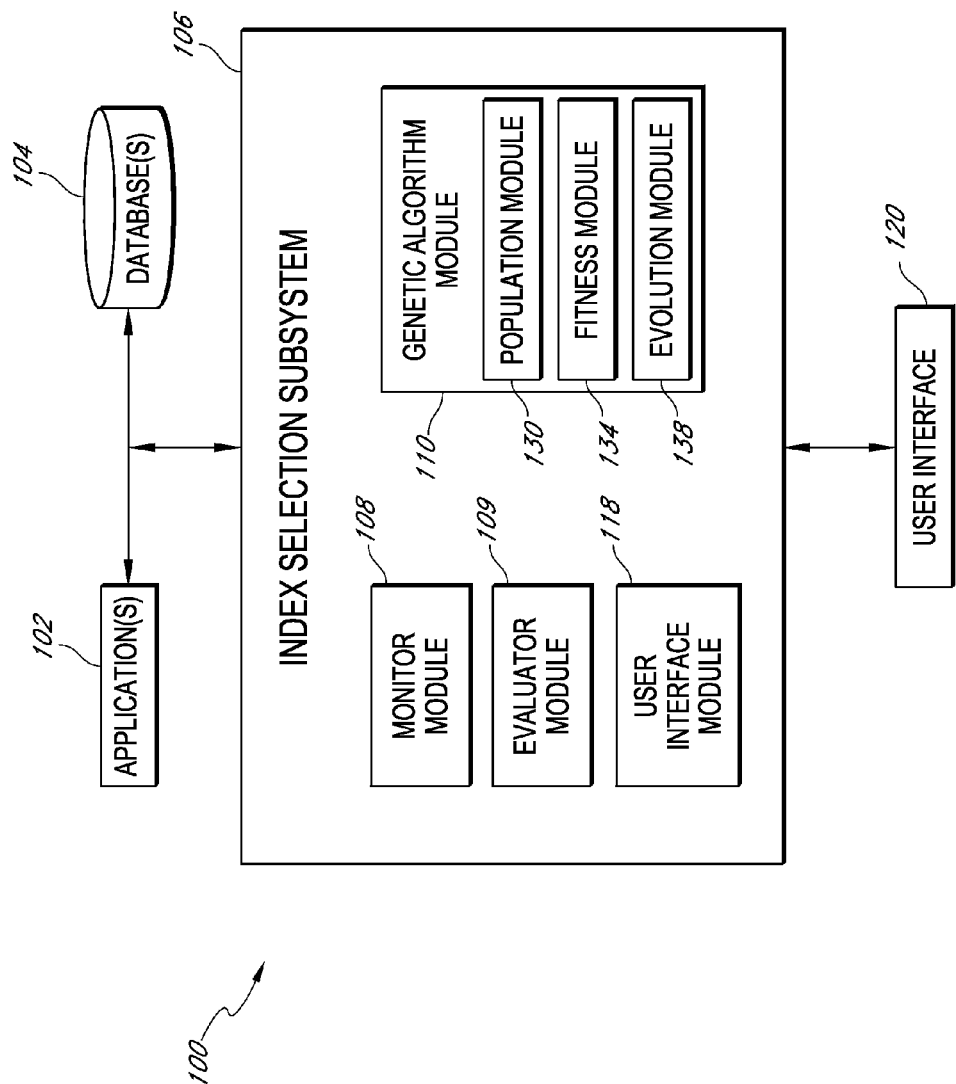
FIG. 1 illustrates a block diagram of an example of a system that uses a genetic algorithm for generating an index configuration for a collection of data such as, e.g., a database.

Various features of the systems and methods will now be described with reference to the drawings described above. Throughout the drawings, reference numbers are re-used to indicate correspondence between referenced elements. The drawings, associated descriptions, and specific implementation are provided to illustrate embodiments of the invention and not to limit the scope of the disclosure.

DETAILED DESCRIPTION

Embodiments of systems and methods are described that can be used to generate an index configuration (e.g., a set of one or more indexes) to improve the overall performance or efficiency of a group of transactions in a collection of data such as, e.g., a database. A transaction includes, but is not limited to, any atomic interaction with a database or other data repository. For example, "database transactions" can include individual Structured Query Language (SQL) statement executions, multiple SQL statements (e.g., SQL statements that are grouped to succeed or fail as a unit), and/or stored procedure calls. Various embodiments can further be applied to other types of computer transactions, such as, for example, method calls (e.g., JAVA method calls), hypertext transfer protocol (HTTP) requests, queries to a search engine, events, disk storage interactions, or the like, without departing from the scope of the disclosure. Overview of the Index Selection Problem Generating a set of indexes for multiple SQL statements is a computationally challenging problem and has been showed to be an NP-complete problem (the "Index Selection problem"). Some solutions to the Index Selection problem are designed as a rule based engine that uses human knowledge to narrow down the search space of index candidates. A possible disadvantage of some of these algorithms is that the algorithm cannot fully recognize the database SQL optimizer behavior and its evolution from version to version because of the limited initial indexes candidates. Hardcoded selection criteria used by many of these solutions do not provide index solutions that are better than those provided by a good human database administrator (DBA).

In order to illustrate a possible example of the problem of finding good index candidates, the following are used as three examples of SQL statements for a database with an Employee table and a Department table:

```
Select a.emp_name from employee a, department b
Where a.emp_dept=b.dpt_id
Select a.emp_name from employee a, department b
Where a.emp_dept=b.dpt_id
  And a.emp_salary<50000
Select a.emp_name from employee a, department b
Where a.emp_dept=b.dpt_id
And dpt_avg_salary between 45000 and 50000
```

One possible objective for an Index Selection algorithm is to analyze these three example SQL statements and find an index configuration that can make these three SQL statements execute faster, have reduced input/output (I/O), and/or perform more efficiently on computer hardware. If human knowledge were used to solve this problem based on the above three example SQL statements, the following columns from these two tables might be explored as possible index candidates:

Employee table: emp_name, emp_dept, emp_salary
Department table: dpt_jd, dpt_avg salary In some cases, systems and methods can try each combination (including concatenated indexes) of the index configuration generated from the above index candidates without concern about the selection order. The follow candidates could be explored in some cases in this example:

```
Case 1. Non-concatenated index selection permutation example:

P(any 1 candidate selected) + P(any 2 candidates selected) + P(any 3
candidates selected) + P(any 4 candidates selected) + P(5 candidates
selected)
= 5+5!/3!/2!+5!/2!/3!+5!/1!/4!+1
= 5+5×4/2+5×4×3/(3×2)+5×4×3×2/(4×3×2)+1
= 5+10+10+5+1
= 31
```

```
Case 2. Concatenated for 2 and 3 candidates index selection
              permutation example:

Any 2 and 3 candidates from Employee table
P(3,2)=3!/2!=3
P(3,3)=1
Any 2 candidates from Department table
P(2,2)=1
```

In this illustrative example, the overall possible combination of index configurations for the three example SQL statements is at least 31+3+1+1=36, and this number could increase because permutations have not been counted for Case 1 and Case 2. In a typical production application database, there are likely to be hundreds of tables and thousands of SQL statements. The potential index configuration can be huge. Thus, finding the best indexes or nearly the best index configuration is a challenging problem. Accordingly, embodiments of the index selection technology disclosed herein use a genetic algorithm to efficiently search for an improved or optimal index configuration for a database.

In addition to addressing the problem of the larger number of index candidates that can be generated from hundreds of tables and thousands of SQL statements, certain embodiments of the disclosed index selection technology advantageously may address some or all of the following problems and/or features:

1. Provide a recommendation when to drop indexes.
2. Have relatively few or no hardcoded rules to limit the selection of potential columns as index candidates.
3. Have relatively few or no hardcoded rules to limit the combination of columns in a composite (concatenated) index.
4. Have the ability to use an SQL execution plan as one possible feedback or the only feedback in evaluating a new index. In some implementations, limited or no human preset knowledge is used to limit potential changes of the database optimizer behaviour from version to version.
5. Provide self-balancing between the new recommendation's overhead and total resource reduction.
6. Support SQL workload based index recommendations.
7. Have the capability to return recommendations within a reasonable time.
8. Have the capability to retain knowledge after termination to provide an interim solution and be equipped with learning ability to quickly react to factors including, e.g., SQL workload, change of database structure, and/or change of user behaviour in a production database.
9. Provide CPU, I/O, and/or overall cost reduction searching criteria.

Examples of Index Selection Systems Using Genetic Algorithms

In view of the foregoing, certain embodiments of the systems and methods described herein utilize a genetic algorithm to efficiently search for index configurations for a target database. FIG. 1 illustrates a block diagram of an example of a system 100 that uses a genetic algorithm for generating an index configuration for a collection of data such as, e.g., a database. As shown, the system 100 includes one or more applications 102 that communicate with one or more databases 104. In certain embodiments, the application(s) 102 comprise client programs that connect to a database management system (DBMS) to provide users with the ability to interact with the data of the databases 104, such as, for example, to select, modify, organize, delete, or the like, some or all of the foregoing data. Examples of application programs include payroll or inventory programs, online stores, or the like.

The database 104 can comprise any collection of information or data organized in a way that computer programs can quickly access or select desired portions of the collection. Example DBMSs for use with such databases 104 include those commercially available from Oracle Corporation, IBM, or the like.

The system 100 comprises an index selection subsystem 106 that can generate a set of indexes for the database(s) 104. In the example system shown in FIG. 1, the index selection subsystem 106 comprises a monitor module 108, an evaluator module 109, a genetic algorithm module 110, and a user interface module 118.

In the illustrated embodiment, the monitor module 108 measures, captures, retrieves, and/or records performance statistics of database transactions associated with the application(s) 102 and the database 104. For example, the monitor module 108 can capture, from time-to-time, executed SQL statements, statistics for index recommendations, or other historical data or information. The statistics can include, but are not limited to, a number of executions of each SQL statement, the amount of computer resources used, e.g., CPU, I/O, temporary space used, elapsed time, and so forth. The evaluator module 109 (or other modules of the index selection subsystem 106) may use the information provided by the monitor module 108.

In certain embodiments, the evaluator module 109 can determine a "cost" of a database transaction such as, e.g., execution of one or more SQL statements. For instance, the evaluator module 109 can measure logical reads associated with a particular SQL statement and/or type or group of SQL statements (e.g., the number of data blocks required to satisfy a SQL statement). In certain embodiments, this cost variable is virtually "noise free" since increases in logical reads generally do not occur unless the SQL statement actually consumes more resources. Furthermore, the logical read rate is generally correlated with both CPU and disk I/O. In some implementations, the evaluator module 109 can evaluate the cost of SQL statements without actually executing the SQL statements.

In yet other embodiments, other or additional cost variables, performance values, or estimates of computing resources can be measured, captured, or determined with respect to a SQL statement. For example, the monitor module 108 may measure or capture an elapsed time, which in turn governs response times and throughputs, for execution of a SQL statement. In certain embodiments, however, this measurement can be "noisy," as it may vary depending on the load placed by other SQL statements and/or on the effectiveness of the database's cache. For instance, a second execution of an identical SQL statement is generally far quicker due to the presence of necessary data in the database cache and a reduced need to parse or optimize the SQL statements a second time.

In yet other embodiments, disk I/O, CPU consumption, or the like can be measured, captured, or tracked (e.g., by the monitor module 108) as performance variables relating to database transaction performance. The evaluator module 109 may determine or evaluate a cost estimate based (at least in part) on a weighted combination of, e.g., CPU and I/O resources used in executing SQL statements. In certain embodiments, the evaluator module 109 can further distinguish between two levels of performance or cost. First, the evaluator module 109 can measure the cost of a single SQL execution ("cost per execution"). Second, the evaluator module 109 can measure the cost of all SQL statement executions ("aggregate cost"). In certain embodiments, increases in the aggregate cost can be caused both by increases in individual SQL statement cost or by an increase in transaction rate. Measurements taken by the evaluator module 109 can be stored as one or more data entries in a memory for future processing and/or manipulation. In some implementations, the evaluator module 109 provides a query optimizer that provides a cost estimate of resources used in executing an SQL statement. For example, one possible query optimizer usable with certain embodiments described herein is the Cost-Based Optimizer (CBO) available from Oracle Corporation, Redwood Shores, Calif.

Cost determinations made by the evaluator module 109 can be used by the genetic algorithm module 110 for determining an improved or optimized index configuration for some or all of the database(s) 104. For example, as will be further discussed below, the cost determinations made by the evaluator module 109 can be used to determine a fitness of a gene or chromosome. Although the implementation schematically shown in FIG. 1 utilizes a monitor module 108 and an evaluator module 109, this is not a requirement, and in other implementations some or all of the functionality of the modules 108 and 109 may be shared, merged, or combined in a single module or in multiple modules.

In the embodiment illustrated in FIG. 1, the genetic algorithm (GA) module 110 implements a genetic algorithm to efficiently search for index configurations for a target database such as, e.g., one or more of the database(s) 104. In the illustrated embodiment, the GA module 110 comprises a population module 130 that can generate a population of chromosomes that represent possible index configurations for one or more of the database(s) 104. The chromosomes comprise "genes" that represent, for example, a column in a table in the database, dropping an index from a table in the database, and/or a composite index for the database. The GA module 110 also comprises a fitness module 134 that can determine the "fitness" of the index configurations encoded by the chromosomes. For example, the fitness of a chromosome may be a function of the cost (e.g., measured by the evaluator module 109) for SQL transactions on the indexed database. The GA module 110 may also include an evolution module 138 that implements the genetic algorithm used to "evolve" the population of chromosomes in order to increase or optimize the fitness of the population of chromosomes that represent the possible index configurations. The evolution module 138 may perform mutation, crossover (recombination), inheritance, and selection operations to evolve chromosomes from one population to the next population with increased fitness. Some embodiments of the GA module 110 use virtual indexing to simulate building an index, which may improve performance since the index is not actually built for the database.

The evolution module 138 can continue the evolution until a termination criterion (or criteria) is met, for example, a maximum number of generations (e.g., 100 generations), a maximum computer processing time, a maximum amount of computer resource usage (e.g., I/O), a time-of-day, and/or a satisfactory level of fitness is found. In some embodiments, the evolution module 138 may continue "evolving" index solutions as new SQL statements, tables, and/or columns of tables are created for the database(s) 104. The GA module 110 may output (e.g., via user interface module 118) information related to the set of indexes that are most "fit" at a particular time. As one possible example, a DBA may request that the GA module 110 provide each day at a time (or times) that is helpful for the DBA to handle daily operations (e.g., 4:00 pm) the most fit indexes (at that time or times) for the database(s) 104. Accordingly, a possible advantage of such embodiments is that the index selection subsystem 106 provides an automated process for improved or optimal index management for the database(s) 104.

In some embodiments of the GA module 110, the length of the chromosome and/or the number of chromosomes can be allowed to increase (or decrease) during the evolution. In some embodiments, chromosomes for candidate indexes can be encoded using a conventional bitmap of binary digits (which may use thousands of bits to represent an index configuration). In other embodiments, chromosomes can be advantageously encoded using a non-bitmapped representation of the index configuration, which may in some cases improve performance compared to a bitmapped representation. In some embodiments, chromosomes may include genes to represent one or more of the following: a column in a table in the database, dropping an index from a table in the database, and/or a composite index for the database. In some embodiments, the population module 130 may use a participation pool to select more fit genes to be included in the initial population of chromosomes, which may reduce the time for finding an improved or optimal solution. In some embodiments, the population module uses a probabilistic method for determining the length of a potential composite index (which comprises two or more columns from a table). Some implementations of the GA module 110 use one, some, or all of the following: (i) growing chromosomes in length and/or in number during the evolution, (ii) non-bitmapped encodings for chromosomes, (iii) a participation pool for the genes, and (iv) a probabilistic method for constructing a composite index.

In some implementations, the GA module 110 can be configured to "learn" from prior generation(s) of chromosomes that were evolved to provide an index configuration for the database(s) 104. For example, the GA module 110 may store information related to one or more prior generations of chromosomes, index configurations, and so forth and the evolution module 138 may restart an evolution based at least in part on such information. Therefore, such implementations advantageously learn from prior evolution and may be able to find an updated index configuration more efficiently than starting from, e.g., a random initial population of chromosomes.

The user interface module 118 can communicate information to and/or receive information from a user (or a user computing system) via a user interface 120. For instance, the user interface module 118 can inform a user through the user interface 120 when one or more indexes for the database(s) 104 are generated. Therefore, such implementations advantageously learn from prior evolution and may be able to find an updated index configuration more efficiently than starting from a random initial population.

In certain embodiments, the user interface 120 comprises a display. The user interface 120 may interact with the index selection subsystem 106 via wired or wireless network. Further, in certain embodiments, the user interface 120 can be associated with a computer device on which one or more of the application(s) 102 executes. The user interface 120 may be used by a DBA to monitor or interact with the genetic algorithm module 110.

In certain embodiments, the index selection subsystem 106 comprises one or more server computers for executing one or more of the components described above. In yet other embodiments, components of the index selection subsystem 106 can execute on other types of computer devices, such as, for example, personal computers, workstations, virtual computing systems, portable computing devices and the like.

Embodiments of the index selection subsystem 106 can be used for applications other than the Index Selection problem. For example, in other embodiments, the index selection subsystem 106 can be used for other database configuration recommendations such as determining materialized views and/or table partitions for a target database. In other implementations, embodiments of the systems and methods disclosed herein may be used to search a search space for a solution to combinatorial optimization problem other than the Index Selection problem such as, e.g., a routing problem, a constraint satisfaction problem, and so forth.

Examples of Index Selection Methods Using Genetic Algorithms

Figure 2:
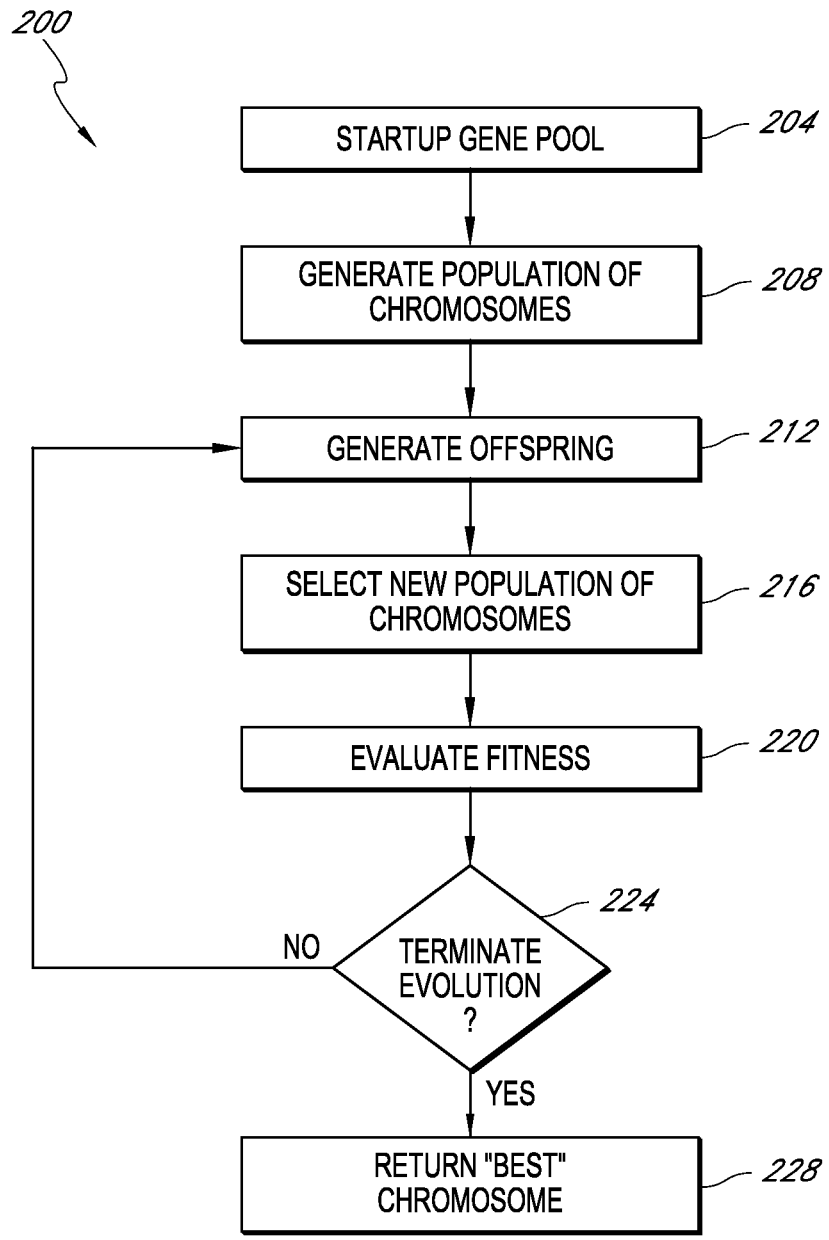
FIG. 2 illustrates a flow chart of an example method that uses a genetic algorithm to generate an index configuration for a collection of data such as, e.g., a database.

FIG. 2 illustrates a flow chart of an example method 200 that uses a genetic algorithm to generate an index configuration for a collection of data such as, e.g., a database. The index selection subsystem 106 (e.g., the GA module 110) may implement at least portions of the example method 200. Further details of the example method 200 will be described below.

At block 204, the example method 200 begins with a startup gene pool. The startup gene pool can include genes that encode index candidates for a database. Index candidates can include, but are not limited to, a column in a table in the database, dropping an index from a table in the database, and/or a composite index for the database (a composite index covers more than one column of a table). In some cases, the startup gene pool is generated for a database and represents an initial gene pool from which chromosomes are selected and "evolved" to determine a "best" chromosome, e.g., a chromosome comprising genes that encode an index configuration that has the best fitness (e.g., relatively low "cost") for the database.

At block 208, a population of chromosomes is generated from the genes in the genes pool. In some embodiments, as will be discussed, a participation probability is used to fill the genes in the population of chromosomes. The participation probability may be based at least in part on the cost of an index candidate encoded by a gene. In other embodiments, the population of chromosomes includes chromosomes determined from the results of a prior evolutionary calculation for a database. Thus, in some such embodiments, the method 200 includes the ability to "learn" from the prior evolution and advantageously need not start from, e.g., a random initial population of genes. At block 208, the fitness of each of the chromosomes in the population may be determined (or may be provided from the results of a prior evolution). For example, the fitness of a chromosome that represents an index configuration for a database can be measured by the cost of computer resources used for executing SQL statements in the indexed database. In some implementations, the evaluator module 109 can determine the fitness (e.g., cost) for each of the chromosomes in the population.

At block 212, offspring are generated from the chromosomes in the population of chromosomes from block 208. As will be further described below, offspring can be generated by mutating genes in parent chromosomes (and/or offspring chromosomes), combining parent chromosomes using crossover techniques, and so forth. At block 216, a new population of chromosomes is selected from chromosomes in the parent population (from block 208) and/or chromosomes in the offspring population (from block 212). In some implementations, the new population is selected based at least in part on the fitness of the parent and/or offspring chromosomes. For example some implementations used elitism, wherein one or more of the parent chromosomes with the highest fitness are included in the new population of chromosomes. In some implementations, a number of the most fit chromosomes from the offspring or parent populations are included in the new population.

At block 220, the fitness of the chromosomes in the new population is evaluated. The fitness may be based at least in part on the cost of the index configurations encoded by the chromosomes. At block 224, the method 200 can determine whether to terminate the evolution of the population of chromosomes according to one or more termination criteria. For example, in various embodiments, the termination criteria can include one or more of the following: a maximum number of generations (e.g., 100 generations), a maximum computer processing time, a satisfactory level of fitness has been reached, an output time has been reached when a DBA desires to receive the "best" index configuration identified as of the output time, etc. If the method 200 determines that the evolution should continue, the method 200 returns to block 212, where a new population of offspring is generated.

If the method 200 determines that the evolution should be terminated, at block 228, the "best" chromosome (according to the fitness criterion) can be returned. For example, the user interface module 118 may output (e.g., via the user interface 120) information related to the status of the evolution when terminated. This information may include (but is not limited to) the best-so-far index configuration identified during the evolution, parameter associated with the evolution (e.g., number of generations, fitness, number and/or length of the chromosomes, or other characteristics of the population pool). The method 200 may store (e.g., in persistent storage) information associated with the population of chromosomes so that the evolution may be restarted from that point.

Figure 3A:
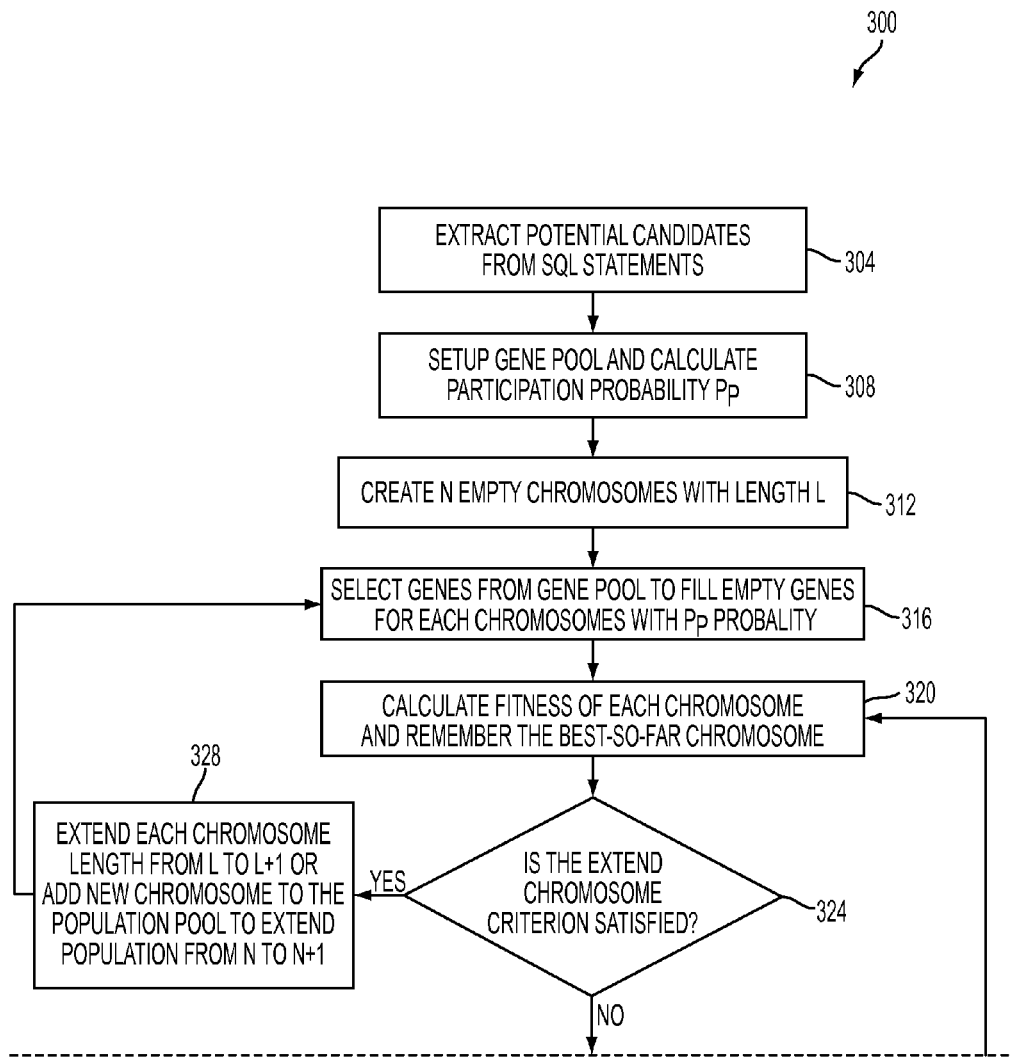
FIGS. 3A-3B illustrate a flow chart of another example method that uses a genetic algorithm to generate an index configuration for a collection of data such as, e.g., a database.
Figure 3B:
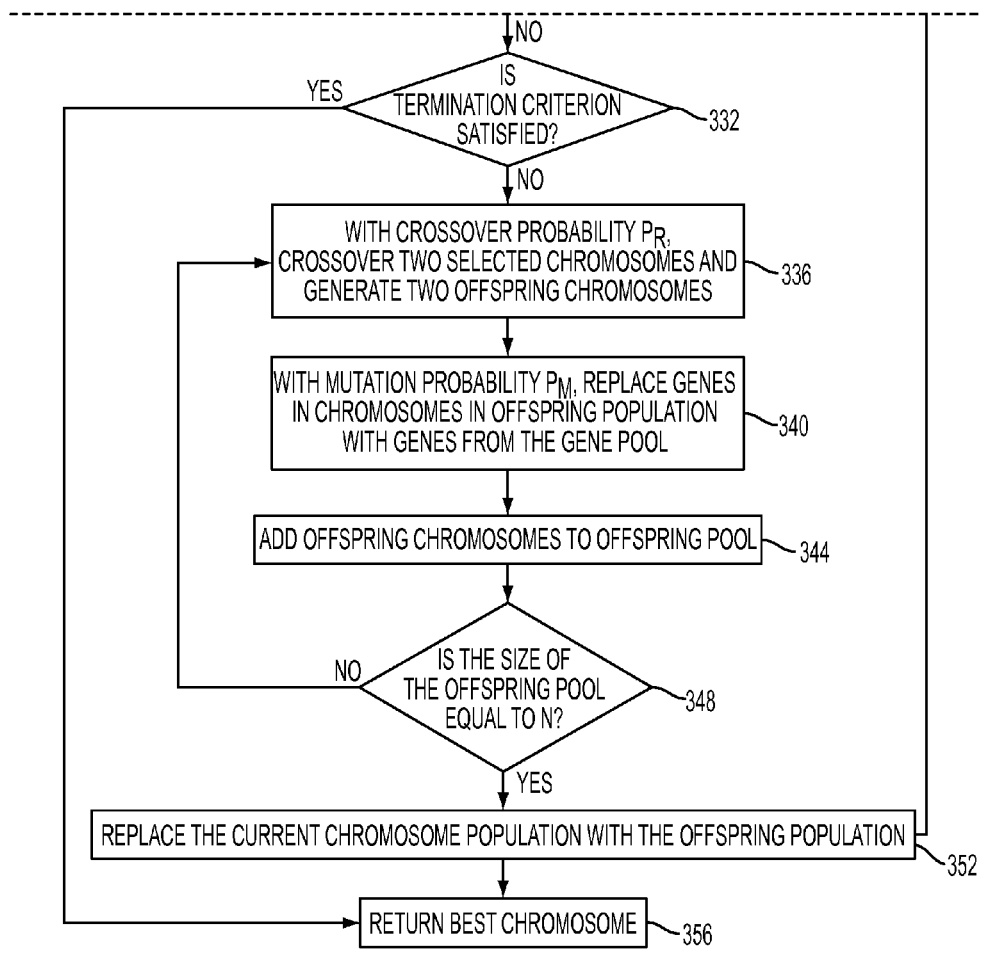

FIGS. 3A-3B illustrate a flow chart of another example method 300 that uses a genetic algorithm to generate an index configuration for a collection of data such as, e.g., a database. Some features of the example method 300 may be generally similar to features of the example method 200 described with reference to FIG. 2. Embodiments of the example method 300 may be implemented by the index selection subsystem 106 described with reference to FIG. 1.

A. Examples of Gene and Chromosome Encoding

For some Genetic Algorithms, a bit string (e.g., a bitmap) is used to represent the genes and/or chromosomes in the solution space. For a consecutive space search like numeric solution, the binary representative of a bit string may be embedded with the direction of the searching behavior during crossover and mutation For index genes, the bitmap binary relationship may not, in some cases, provide benefits during crossover and mutation. Also, in some implementations, thousands of index candidates (genes) may be used in a chromosome. In some implementations that adopt a bitmap string as the gene encoding mechanism, the outcome chromosomes may be too big for crossover and mutation. Such implementations of the genetic algorithm may have an overall performance that is similar to a random search. Therefore, in order to achieve certain benefits of the genetic algorithm for the index selection problem, embodiments of the systems and methods may encode a gene comprising an index candidate using an identifier. For example, the gene may encode the index candidate's name. The following example illustrates a Chromosome A having 4 genes encoded using the index candidate names (rather than a bitmap).

| Chromosome A | | | |
| --- | --- | --- | --- |
| T1.C1 | T2.C1 | Drop T1.index1 | (T1.C2,T1.C3) |

In this example, T1.C1 means that column C1 of table T1 is selected as a gene in the Chromosome A, T2.C1 means that column C1 of table T2 is selected as a gene in the Chromosome A, Drop T1.index1 means that dropping index1 from table T1 is selected as a gene in Chromosome A, and (T1.C2, T1.C3) means that a composite index with columns ordered as C2,C3 of table T1 is also selected as a gene in Chromosome A. In some embodiments, an object identification number (e.g., object ID) of an object in the database can be used to encode index candidates. Also, in some such embodiments, a specific order of genes in a chromosome may bespecified based (at least in part) on object ID, which may, in some cases, allow better genes to be carried over from generation to generation.

Therefore, in various implementations, the identifier used to encode an index candidate in a gene may be a data structure comprising a string of alphabetical characters, numerical characters, alphanumeric characters, and the like.

A. Example Method for Composite Index Construction

Since the overhead of a long composite index is higher than that of a short composite index, and it may be disadvantageous to hardcode the length L of each potential composite index in a chromosome, certain embodiments use a probabilistic method for determining length L 2 of potential composite index candidates. For example, in certain such embodiments, a probability distribution P(L) for lengths L of candidate composite indexes may be used (at least in part) to select the length of a potential composite index candidate. The probability distribution P(L) may be a decreasing function as length L increases, at least over a range of possible lengths. For example, $P(L_1) > P(L) > P(L_2)$, for lengths L in the range $L_1 < L < L_2$.

In the following non-limiting, illustrative example, assume that potential candidates for a composite index potential are: Table T with seven column candidates: C1, C2, C5, C3, C8, C10, and C9. In some embodiments, any number from 2 to 7 of these columns from the candidate pool can be selected to build a composite index by placing the columns in various orders. If, for example, the maximum length of a composite index is M (less than or equal to 7 in the above example for Table T), certain embodiments use the following formulas to determine the probability P(L) of the potential length L of composite index candidates, for 2 L M. The weight, W(L), of each potential length L for a candidate composite index can be determined, in some embodiments, as follows. The probability P(L) can be determined from the weight W(L) in this example.

$$W(L) = (M^2 - D*L^2)$$
$$TotalW = Sum(W(L), \text{ from } L=2 \text{ to } M)$$
$$P(L) = W(L)/TotalW,$$

where D is a decline factor. In some implementations, the default value for the decline factor D is 0.8, although other values can be used such as, e.g., 0, 0.1, 0.2, 0.3, 0.4, 0.5, 0.6, 0.7, 0.9, or 1.0. The decline factor D may be set by a user or the index selection subsystem. In some implementations, the subsystem can adjust the decline factor D (upward and/or downward) during the genetic evolution. For example, if the fitness is not improving after a number of generations, the subsystem may decrease the decline factor D so that longer composite index candidates can be used.

In implementations using declining probabilities, the probability of getting a longer length L for the composite index will be lower, although it can still be possible to get a long composite index (e.g., up to the maximum length M), since the probabilities are not zero. The decline factor D is a configurable parameter that can be adjusted to provide a desired distribution of lengths. If a relatively high decline factor that is close to 1 is used, the above formula creates a rapidly declining probability that a longer length of composite index will be created. Therefore, in such a case, the probability that a shorter length composite index will be selected is relatively high. If a relatively low decline factor D, closer to 0, is used in the formula, the probabilities for different lengths L are approximately equal to each other, and generating composite indexes of any length (up to the maximum length M) is possible. Other formulas for the probability P(L) can be used, and the foregoing are merely examples. For example, if relatively long composite indexes were desired, a probability that increases with L could be used.

Once the lengths of one or more composite index candidates are determined, a participation probability (described in more detail herein) can be used to select columns from the candidate columns to fill the composite index. See, e.g., the illustrative example described below with reference to Table 4. A column having a higher participation probability will have a higher chance to take the first position in the composite index, and so forth. An advantage of certain implementations is that it not only aligns with human DBA knowledge, but at the same time it keeps open the possibility that columns having a relatively low participation probability can nevertheless be selected to take the first few positions in a composite index. This may increase the diversity of the population.

B. Examples of an Initial Gene Pool

At block 304 of the example method 300, potential index candidates are extracted from a group of SQL statements. For example, for each SQL statement, a column sensitive SQL parser is used to extract columns from the SQL statements. In some embodiments, if there are any existing indexes that are shown in the execution plan (or query plan) for the database, the existing indexes will also be extracted by the parser. The following, non-limiting, illustrative Table 1 shows five example SQL statements and eight example tables (A, B, C, D, F, G, I, K), although fewer or more statements or tables can be used in other examples and applications.

TABLE 1

| SQL Si | Tables Si.Ti | Index Candidates Si.Ti.Ci | Drop Index Candidates Si.Ti.Di |
|---|---|---|---|
| SQL1 | A,B,C | (A.F1,A.F2,A.F3) A.F1 A.F2 A.F3 B.F2 C.F3 | A.ind1 B.ind3 C.ind2 |
| SQL2 | B,D | B.F2 D.F3 D.F4 | B.ind3 D.ind2 |
| SQL3 | F,G | (F.F1,F.F2) G.F4 F.F1 F.F2 | G.ind4 |
| SQL4 | A,C | A.F2 C.F3 | |
| SQL5 | I,K | I.F1 I.F2 K.F4 | I.ind5 |

In the above example Table 1, (A.F1,A.F2,A.F3) and (F.F1,F.F2) are composite (or concatenated) index candidates comprising two or more columns of a table, and the Drop Index Candidates column are indexes used by that SQL statement only.

Most relational database management systems (RDBMS) provide virtual indexing and virtual index dropping (e.g., disable index) functions. Virtual indexing can be used to test potential new indexes prior to actually building the index in the database. Since actually building indexes for a database can be computationally resource intensive, virtually building the indexes can provide significant computation performance efficiencies for certain embodiments of the methods 200 and 300. As discussed above, embodiments of the disclosed systems and methods search for and find index configurations for a database that may provide reduced or lowest cost in terms of computer resources, which advantageously can increase database performance and efficiency and provide improved management of computer resources for the RDBMS. Such performance, efficiency, and resource management increases are some possible examples of further technical effects provided by embodiments of the systems and methods that go beyond normal effects of execution of the systems and methods on computer hardware.

I. Participation Probability

At block 308 of the example method 300, for each candidate gene in a candidate pool, virtual indexing can be used to test the individual candidate's contribution to the overall cost change. For example, in some embodiments, the virtual explain plan function (e.g., explain plan in the RDBMS available from Oracle Corporation, Redwood Shores, Calif.) can be used to build the candidates virtually. Cost of a candidate may be determined by the evaluator module 109 (e.g., by using the CBO in an Oracle implementation). For new indexes, an overall cost reduction may be obtained. For a virtually dropped index, an overall cost increase may occur as shown in Table 2 below.

In the following non-limiting, illustrative Table 2, for each candidate Si.Ti.Ci in the candidate pool, the example method 300 virtually builds the index for that specific column or virtually drops the index, and then executes the virtual explain plan function for the SQL statements so as to calculate a total cost change if the candidate Si.Ti.Ci is virtually built. In this example, the total cost change is denoted by Change$i$ and is determined as follows:

Change$i$ = Sum(cost of SQL$i$(after)) −   /* after Si.Ti.Ci is virtually built */
   Sum(cost of SQL$i$(before))    /* before Si.Ti.Ci is virtually built */

TABLE 2

| SQL Si | Tables Si.Ti | Candidate Pool Index & Drop Index Candidates Si.Ti.Ci | Total Cost Change Change$i$ | Remark |
|---|---|---|---|---|
| SQL1 | A,B,C | (A.F1,A.F2,A.F3) | −200 | Min(−100, −200, −50) = −200 |
| | | A.F1 | −100 | |
| | | A.F2 | −200 | |
| | | A.F3 | −50 | |
| | | B.F2 | −300 | |
| | | C.F3 | −400 | |
| | | Drop A.ind1 | 100 | |
| | | Drop B.ind3 | 200 | |
| | | Drop C.ind2 | 10 | |
| SQL2 | B,D | B.F2 | −100 | |
| | | D.F3 | −300 | |
| | | D.F4 | −500 | |
| | | Drop B.ind3 | 100 | |
| | | Drop D.ind2 | 120 | |
| SQL3 | F,G | (F.F1,F.F2) | −500 | Min(−200, −500) = −500 |
| | | G.F4 | −230 | |
| | | F.F1 | −200 | |
| | | F.F2 | −500 | |
| | | Drop G.ind4 | 200 | |
| SQL4 | A,C | A.F2 | −400 | |
| | | C.F3 | −100 | |
| SQL5 | I,K | I.F1 | −100 | |
| | | I.F2 | −400 | |
| | | K.F4 | −230 | |
| | | Drop I.ind5 | 200 | |

For a composite index candidate, because the position of each column in the composite index may be significant to the total cost change, certain embodiments do not use the default order to build the virtual composite index for simulation. Instead, in some such embodiments, the most significant individual column's cost change is used to represent the composite index. In some such embodiments, this means that the composite index will not be virtually built, but will use the most significant column's cost change to represent Change $i$.

In certain embodiments, in order to calculate the initial Participation Probability, Pp for each index candidate $i$, Pp$i$, the Total Cost Change, Change$i$, for an index candidate is normalized to a positive value. For example, the normalized value for index candidate $i$ is denoted by N$i$ and may be calculated as:

$$N i = \mathrm{abs}(\max(\text{all of Change} i)) + -1 * (\text{Change} i)$$

In some embodiments, for any N$i$ that equals 0, N$i$ (or Pp$i$) is set to a minimum positive value, which advantageously permits every candidate to have a chance to be selected as a gene in a chromosome. In some embodiments, the minimum positive value is selected as min(Ni where Ni>0)*0.5. In the following non-limiting, illustrative Table 3, the normalized value is shown for the index candidates of Tables 1 and 2

TABLE 3

| SQL Si | Tables Si.Ti | Candidate Pool Index & Drop Index Candidates Si.Ti.Ci | Total Cost Change Changei | Remark | Normalized Value |
|---|---|---|---|---|---|
| SQL1 | A,B,C | (A.F1,A.F2,A.F3) | −200 | 200 + 200 | 400 |
|  |  | A.F1 | −100 | 200 + 100 | 300 |
|  |  | A.F2 | −200 | 200 + 200 | 400 |
|  |  | A.F3 | −50 | 200 + 50 | 250 |
|  |  | B.F2 | −300 | 200 + 300 | 500 |
|  |  | C.F3 | −400 | 200 + 400 | 600 |
|  |  | Drop A.ind1 | 100 | 200 − 100 | 100 |
|  |  | Drop B.ind3 | 200 | 200 − 200 = 0 → 80 * 0.5 | 40 |
|  |  | Drop C.ind2 | 10 | 200 − 10 | 190 |
| SQL2 | B,D | B.F2 | −100 | 200 + 100 | 300 |
|  |  | D.F3 | −300 | 200 + 300 | 500 |
|  |  | D.F4 | −500 | 200 + 500 | 700 |
|  |  | Drop B.ind3 | 100 | 200 − 100 | 100 |
|  |  | Drop D.ind2 | 120 | 200 − 120 (Min of Ni > 0) | 80 |
| SQL3 | F,G | (F.F1,F.F2) | −500 | 200 + 500 | 700 |
|  |  | G.F4 | −230 | 200 + 230 | 430 |
|  |  | F.F1 | −200 | 200 + 200 | 400 |
|  |  | F.F2 | −500 | 200 + 500 | 700 |
|  |  | Drop G.ind4 | 200 | Maximum of Changei 200 − 200 = 0 → 80 * 0.5 | 40 |
| SQL4 | A,C | A.F2 | −400 | 200 + 400 | 600 |
|  |  | C.F3 | −100 | 200 + 100 | 300 |
| SQL5 | I,K | I.F1 | −100 | 200 + 100 | 300 |
|  |  | I.F2 | −400 | 200 + 400 | 600 |
|  |  | K.F4 | −230 | 200 + 230 | 430 |
|  |  | Drop I.ind5 | 200 | Maximum of Changei 200 − 200 = 0 → 80 * 0.5 | 40 |

Accordingly, in the illustrative example shown in Table 3, although the cost changes range from −500 to 200, the normalized values range from the minimum positive value of 40 to 700.

For some implementations of the method 300, a random number can be used to setup the initial population of genes in the startup gene pool. However, this can lead to possible disadvantages for a large pool of genes such as, e.g., for the problem of finding an index configuration for a database having many tables and many SQL statements. For example, it is believed the computational time spent for an evolution can be relatively long if a random initial gene pool is used. Therefore, in some implementations of the disclosed systems and methods, the initial gene pool is generated using a Participation Probability, denoted by Pp. Some such implementations advantageously can quickly select better genes for the initial gene pool and can shorten the time the method uses to find better chromosomes in the first few generations.

In some embodiments, the Participation Probability is determined at least in part on the Normalized Values, Ni. For example, the Participation Probability for SQL statement i may be calculated as:

$Ppi = Ni/\text{Sum}(Ni)$.

This value for the participation probability for index candidate i can be used to determine the initial population and during later stages to fill empty gene (e.g., if new chromosomes are added, chromosome lengths are extended, etc.).

The following non-limiting, illustrative Table 4 provides an example of Participation Probabilities calculated by the foregoing formula.

TABLE 4

| SQL Si | Tables Si.Ti | Candidate Pool Index & Drop Index Candidates Si.Ti.Ci | Total Cost Change Changei | Normalized Value Ni | Participation Probability Ppi |
|---|---|---|---|---|---|
| SQL1 | A,B,C | (A.F1,A.F2,A.F3) | −200 | 400 | 0.044444444 |
|  |  | A.F1 | −100 | 300 | 0.033333333 |
|  |  | A.F2 | −200 | 400 | 0.044444444 |
|  |  | A.F3 | −50 | 250 | 0.027777778 |
|  |  | B.F2 | −300 | 500 | 0.055555556 |
|  |  | C.F3 | −400 | 600 | 0.066666667 |
|  |  | Drop A.ind1 | 100 | 100 | 0.011111111 |
|  |  | Drop B.ind3 | 200 | 40 | 0.004444444 |
|  |  | Drop C.ind2 | 10 | 190 | 0.021111111 |
| SQL2 | B,D | B.F2 | −100 | 300 | 0.033333333 |
|  |  | D.F3 | −300 | 500 | 0.055555556 |
|  |  | D.F4 | −500 | 700 | 0.077777778 |
|  |  | Drop B.ind3 | 100 | 100 | 0.011111111 |
|  |  | Drop D.ind2 | 120 | 80 | 0.008888889 |
| SQL3 | F,G | (F.F1,F.F2) | −500 | 700 | 0.077777778 |
|  |  | G.F4 | −230 | 430 | 0.047777778 |
|  |  | F.F1 | −200 | 400 | 0.044444444 |
|  |  | F.F2 | −500 | 700 | 0.077777778 |
|  |  | Drop G.ind4 | 200 | 40 | 0.004444444 |
| SQL4 | A,C | A.F2 | −400 | 600 | 0.066666667 |
|  |  | C.F3 | −100 | 300 | 0.033333333 |
| SQL5 | I,K | I.F1 | −100 | 300 | 0.033333333 |
|  |  | I.F2 | −400 | 600 | 0.066666667 |
|  |  | K.F4 | −230 | 430 | 0.047777778 |
|  |  | Drop I.ind5 | 200 | 40 | 0.004444444 |
|  |  |  |  | Sum(Ni) = 9000 | Sum(Ppi) = 1 |

At block 312 of the example method 300, the initial population may be setup with a relatively small number N of chromosomes each comprising a relatively small number L of genes (L represents the length of the chromosome). In this example, each chromosome encodes a potential index configuration for the target database. In some embodiments, the chromosome length L may be extended step-by-step during the genetic evolution. In some implementations, an indicator to extend the length of the chromosome can be the performance of a fitness function value. For example, if there is no more gain in the fitness after multiple generations, the best solution may have already been found for the current small size of the index configuration. For example, if a pool of 4-gene chromosomes that evolved for hundreds of generations and come to a stage that the fitness function value cannot be improved, the best 4 index configurations may have been found. In some implementations, the length of a chromosome can be extended to, for example, 5 or 6 genes in order to look for a broader coverage solution for more SQL statements. Other chromosome lengths can be used in other embodiments. For example, the chromosome length (in terms of number of genes) may be 1, 2, 3, 7, 8, 9, 10, 15, 25, 50, 70, 100, 500, 1000, 5000, or more. Also, in various implementations, the number of chromosomes can be different. For example, 1, 2, 3, 4, 5, 6, 7, 8, 9, 10, 20, 75, 125, 500, 1000 or more chromosomes can be used.

In one possible non-limiting example, the evolution starts with an initial gene pool of four chromosomes, and each chromosome has 4 genes. In this example, 4 index configurations will be recommended at the initial stage of the evolution. If the evolution is executed for a greater length of time, then, in some implementations, the chromosomes can be extended in length up to a maximum length. In some implementations, the maximum length is a user configurable parameter or may be automatically adjusted by the system during evolution.

At block 316 of the example method 300, the chromosomes are filled based on the potential candidates determined at block 304. In one implementation, in the initial generation denoted by Gen(0), the genes of each chromosome are initially empty. The empty genes in the initial generation are filled based at least in part on the participation probability of the genes in the gene pool, e.g., the likelihood that an empty gene is filled with index candidate i is Ppi In some embodiments, a selected candidate from the gene pool will not be used again by any other chromosome in the Gen(0) population (e.g., the gene is removed from the gene pool when filled in a chromosome), which may increase the likelihood that the Gen(0) chromosomes have a higher variety of genes in the initial population. If an empty gene occurs during evolutionary operations such as, e.g., mutation, extension of the length of a chromosome, or adding a new chromosome to a population, the empty gene can be filled using the participation probability in some implementations.

Accordingly, in various embodiments, the gene selection criteria used at block 316 include, but are not limited to, one or more of the following: (1) for each empty gene, use the participation probability to select a gene from the gene pool to fill an empty gene in a target chromosome; (2) remove the gene from the gene pool once it has been selected by any chromosome; (3) drop indexes are included in the gene pool so that drop indexes can be a solution for the index configuration; and (4) if a composite index is selected, the composite index construction method described herein may be used to compose the composite index.

One possible non-limiting, illustrative example of composing a gene representing a composite index will be described. In this example, the composite index candidate (A.F1, A.F2, A.F3) from Tables 1-4 is selected (e.g., based on its participation probability). The composite index construction method described above can be used to determine the length of the composite index and the order of the columns in the composite index based on the selected composite index candidate. In this example, the length of the composite index candidate is L=3, therefore the probabilities P(2) and P(3) for lengths L=2 and L=3 of the composite index are calculated. Continuing with this example, if P(2)=0.6 and P(3)=0.4, it is more likely (but not required) that a composite index of length L=2 will be selected. Assuming, in this example, that the length L=2 is selected, the participation probabilities of the columns in the composite index candidate (e.g., A.F1, A.F2, and A.F3) can be used to determine which will be the first column and which will be the second column in the composite index. Continuing with this example, Table 4 shows the participation probabilities for these three columns are (approximately) Pp(A.F1)≈0.033, Pp(A.F2)≈0.044, and Pp(A.F3) ≈0.028. For these example participation probabilities, it is more likely (but not required) that the column A.F2 will be selected to be the first column of the composite index and the column A.F1 will be selected to be the second column of the composite index. Therefore, in this illustrative example, the gene will be filled with the composite index (A.F2, A.F1). In other examples, the length of the composite index and/or order of the columns in the composite index may be different.

C. Examples of Determination of Fitness

At block 320 of the example method 300, for each chromosome, the genes (e.g., index configurations) may be virtually applied in a chromosome in order to calculate the fitness. For example, the method may perform an explain plan for the SQL statements to determine the execution plan that the RDMS can follow to execute the SQL statements. In some embodiments, the minimum positive value discussed above (with reference to the normalized value Ni) is used to represent how much the total cost can be reduced by this chromosome (e.g., index configuration).

The fitness function value for chromosome(i) is denoted by Fit(i). In some embodiments, Fit(i) may be determined based at least in part on the cost of SQL statements (e.g., determined by the evaluator module 109) as:

| | |
|---|---|
| Fit(i) = Sum(cost of SQLi(before)) − | /*Before chromosome is virtually built */ |
| Sum(cost of SQLi(after)) | /* After chromosome is virtually built */ |

In various embodiments, various fitness functions can be adopted to achieve the target of the search. For example, with a CPU bound database application, a fitness function can be based at least in part on a metric to reduce the overall CPU. With an I/O bound application, the fitness function can be based at least in part on I/O. In some embodiments, a weighted combination of CPU and I/O can be used. In some embodiments, the fitness function may be determined using a cost-based SQL optimization algorithm.

As described herein, chromosomes can recombine according to a crossover probability Pr(i) so as to form offspring chromosomes. In some embodiments, the crossover probability for a chromosome i is determined based at least in part on the fitness function for the chromosome. For example, in some embodiments, the crossover probability may be:

$$Pr(i)=Fit(i)/Sum(Fit(i)),$$

where the sum is taken over the number N of chromosomes in the population. In this formulation, chromosomes that are more fit are more likely to be selected for crossover.

Table 5 is a non-limiting example that illustrates a gene pool comprising examples of index candidates and participation probabilities Ppi for the genes in the gene pool.

TABLE 5

| GENE POOL | PARTICIPATION PROBABILITY Ppi |
|---|---|
| (A.F1,A.F2,A.F3) | 0.044444444 |
| A.F1 | 0.033333333 |
| A.F2 | 0.044444444 |
| A.F3 | 0.027777778 |
| B.F2 | 0.055555556 |
| C.F3 | 0.066666667 |
| Drop A.ind1 | 0.011111111 |
| Drop B.ind3 | 0.004444444 |
| Drop C.ind2 | 0.021111111 |
| B.F2 | 0.033333333 |
| D.F3 | 0.055555556 |
| D.F4 | 0.077777778 |
| Drop B.ind3 | 0.011111111 |
| Drop D.ind2 | 0.008888889 |
| (F.F1.F.F2) | 0.077777778 |
| G.F4 | 0.047777778 |
| F.F1 | 0.044444444 |
| F.F2 | 0.077777778 |
| Drop G.ind4 | 0.004444444 |
| A.F2 | 0.066666667 |
| C.F3 | 0.033333333 |
| I.F1 | 0.033333333 |
| I.F2 | 0.066666667 |
| K.F4 | 0.047777778 |
| Drop I.ind5 | 0.004444444 |
| TOTAL | 1 |

Table 6 is a non-limiting example that illustrates an initial generation Gen(0) of four chromosomes each of length four that were selected from the example gene pool illustrated in Table 5. Table 6 also shows the fitness function values Fit(i) and the crossover probability Pr(i) for each chromosome.

TABLE 6

| Gen(0) | Fitness Function Value Fit(i) | Crossover Probability Pr(i) |
|---|---|---|
| A.F1 | 12000 | 0.205479 |
| D.F4 | | |
| B.F2 | | |
| Drop I.ind5 | | |
| B.F2 | 40000 | 0.684932 |
| A.F2 | | |
| I.F1 | | |
| G.F4 | | |
| C.F3 | 400 | 0.006849 |
| F.F1 | | |
| D.F3 | | |
| B.F2 | | |
| A.F2 | 6000 | 0.10274 |
| K.F4 | | |
| (A.F2,A.F1) | | |
| Drop B.ind3 | | |
| Total Fitness = | 58400 | 1 |

In some embodiments, after the calculation of the fitness at block 320, the best chromosome of the current generation is compared with a stored value of the best-so-far chromosome. If the current best chromosome is better than the stored best-so-far chromosome, the current best chromosome is selected to replace the best-so-far chromosome and this updated value for the best-so-far chromosome is stored. In some embodiments, more than one best chromosome is stored, e.g., the best 2, 3, 4, 5, or more chromosomes are stored. The best chromosome(s) can be included in subsequent generations so that the evolution does not lose track of the best solutions identified during the evolution.

Evolution performance can indicate how well the current population is evolving. For example, if values of the fitness function are increasing relatively rapidly, performance of the genetic search algorithm generally may be good.

Various embodiments of the genetic algorithm may utilize one or more criteria to quantify evolution performance.

For example, in certain embodiments, at block 324, two criteria, Criterion 1 and Criterion 2, are used to keep track of the evolution performance. Different criterion or criteria can be used in other embodiments.

Criterion 1: Number of generations after chromosome length extension

In this criterion, the number of generations after length of the chromosome is extended without significant fitness improvement is tracked. If the number of generations is equal to a first threshold value, extending the length of the chromosome is likely providing little or no benefit to the overall performance during the evolution. Therefore, in some embodiments, rather than further extending the length of the chromosome, new chromosomes are added to the population pool. Criterion 1 is satisfied (e.g., "True") if the number of generations is less than the first threshold.

Criterion 2: Number of generations after adding chromosome to the population pool In this criterion, the number of generations after adding the chromosome to the population pool without fitness improvement is tracked. If the number of generations is equal to a second threshold, then adding additional chromosomes to the gene pool may be providing little or no benefit to the evolution performance. Therefore, in some embodiments, extending the length of one or more chromosomes in the gene pool by one (or more) genes may be utilized. Criterion 2 is satisfied (e.g., "True") if the number of generations is less than the second threshold.

The first and second thresholds for Criteria 1 and 2, respectively, may be configurable parameters that may be, for example, defined by a user (e.g., DBA) and/or set by the system before (or during) execution. The thresholds may be adjusted during execution of the program by a user of the system. Also, in other embodiments, only Criterion 1 or Criterion 2 is used but not both criteria. In other embodiments, additional and/or different criteria may be used.

In some implementations, the answer to the question "Is the extend chromosome criterion satisfied?" is "Yes" if either Criterion 1 or Criterion 2 is satisfied or if both Criterion 1 and Criterion 2 are satisfied. In this case, it is likely that extending the length and/or number of chromosomes will lead to further improvement in the fitness function. Therefore, certain embodiments of the method move to block 332 described below and the length and/or number of chromosomes are extended.

In some implementations, the answer to the question "Is the extend chromosome criterion satisfied?" is "No" if both Criterion 1 and Criterion 2 are not satisfied (e.g., the numbers of generations equals the first and second thresholds, respectively). In this case, further extension of the chromosome (in length and/or number) is unlikely to improve fitness, e.g., the best solution may have already been found. Therefore, in such implementations, the method continues to block 332.

D. Examples of Extending the Length of Chromosomes and Adding Chromosomes

As described above, in some embodiments, there may be two ways to extent the chromosome—in length and/or in number. Embodiments of the method 300 may chose to extend the chromosome based at least in part on whether Criterion 1 and/or Criterion 2 are found to be satisfied at block 324.

For example, if Criterion 1 is satisfied, then each chromosome is extended in length from L to L+1. As one example, in a population with L=4, if Criterion 1 is satisfied, L increases to 5. For each chromosome, a new empty gene will be added to the end of the chromosome. This empty gene can be filled by embodiments of the technique described above for block 316. For example, genes may be added based (at least in part) on their participation probabilities.

Continuing with this example, if Criterion 2 is satisfied, then one additional chromosome is added to the population pool to increase the number of chromosomes in the pool from N to N+1. For example, if the current size of the population pool is N=4, then 4 chromosomes in the pool will be used for the evolution. Adding one empty chromosome to the pool will increase the size of the pool to N=5. In some implementations, all the genes in this new chromosome are initially empty and can be filled with genes by the embodiments of the technique described above for block 316. For example, genes may be added based (at least in part) on their participation probabilities.

In other embodiments, the length of the chromosome can be extended by more than one gene. In other embodiments, the size of the population pool can be increased by more than one chromosome. In some implementations, the initial population begins with N=4 and L=4. In other implementations, the user of the system may select value(s) for N and/or L based, at least in part, on the number of SQL statements and/or tables that the index selection subsystem 106 handles (e.g., value(s) for N and/or L may be based at least in part on the size of the search space).

In various embodiments, there can be one or multiple termination criteria. For example, in some implementations, if at least one of the following is satisfied, the method 300 will stop and return the best chromosome as the best index configuration for the target database. Example termination criteria include, but are not limited to, one or more of the following.

1. If both Criterion 1 and Criterion 2 from block 324 are consecutively reaching their respective thresholds, the termination criterion is satisfied.
2. A time limit (e.g., CPU time, elapsed time, etc.) is set and satisfied. For example, a time limit of 20 minutes may be set, and the method will terminate after 20 minutes (elapsed time, CPU time, or combination thereof in various implementations). Other values for time limits can be used.
3. A maximum number of index configurations is set and is satisfied.
4. A fitness improvement target is reached. For example, the fitness improvement target may be an increase in fitness by a first factor (e.g., 30%), or a reduction of cost, CPU time, and/or I/O by a second factor. Other values for fitness improvement targets can be used.

Other termination criteria are possible. For example, the method may terminate when a certain number of generations is reached (e.g., 100 generations), when fitness seems to be reaching a plateau or asymptote and further iterations are unlikely to produce better results, when computer resources (e.g., I/O) have reached a limit, or combinations thereof. In some embodiments, the termination is determined automatically by the system. In other embodiments, some degree of user interaction is used. For example, a DBA may inspect the best chromosome, which represents the best index configuration at a point in the evolution, and determine whether or not to continue the evolution to attempt to find a fitter chromosome (e.g., a better index configuration).

E. Examples of Genetic Evolution Operations

If the termination criterion or criteria at block 332 are not satisfied, the method 300 continues at blocks 336 and 340 in which new offspring of chromosomes are bred using crossover (block 336) and mutation (block 340). In other embodiments, only crossover or only mutation are used. In other embodiments, other genetic operators may be used in addition to or instead of crossover and/or mutation. For example, genetic operators such as regrouping, colonization-extinction, and/or migration may be used in various implementations.

I. Examples of Crossover

Figure 4:
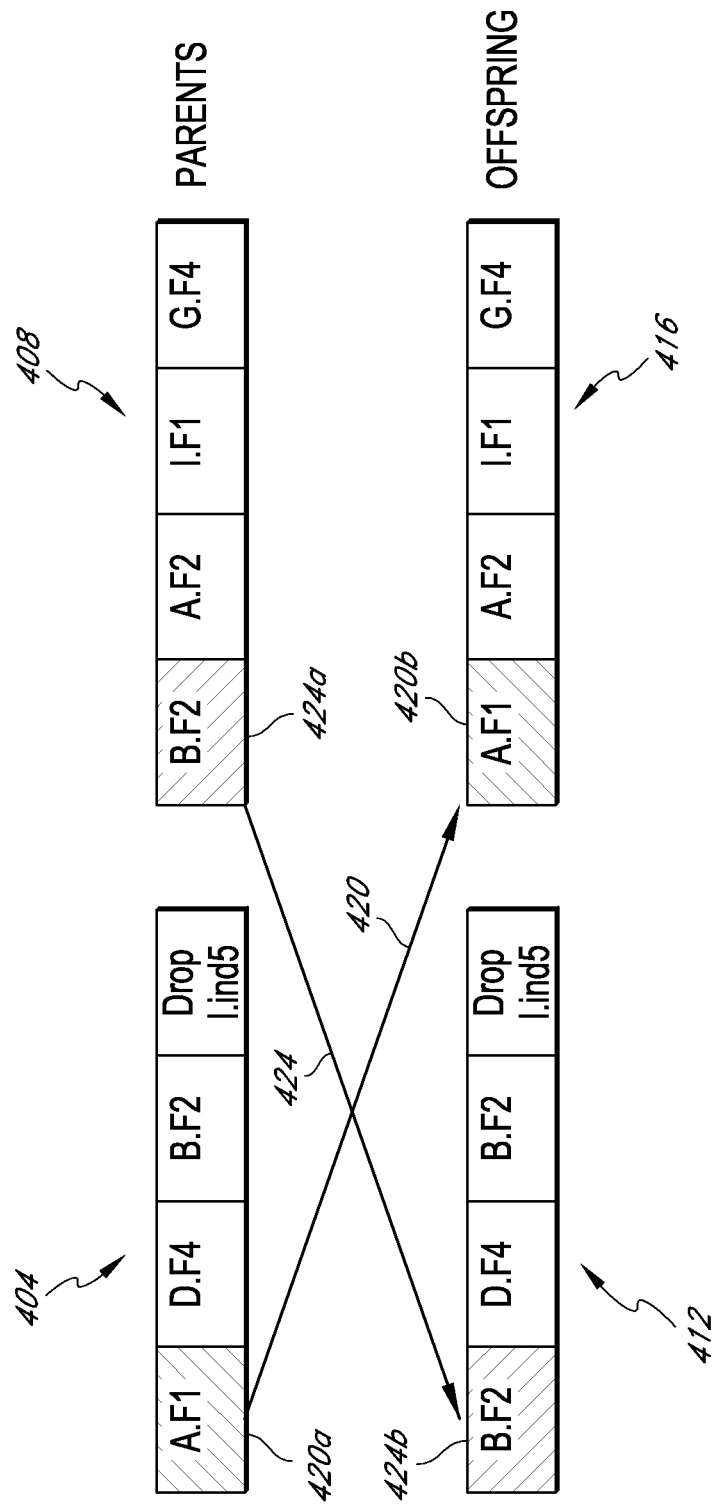
FIG. 4 illustrates an example that shows crossover for two chromosomes.

In one example, any two chromosomes from the current population are selected based at least in part on their respective crossover probabilities Pr(i) and a crossover genetic operator is applied to each chromosome. The crossover probability may be predefined, set by a user, and/or be an adjustable parameter that changes during the evolution (e.g., as fitness of the chromosome changes). FIG. 4 illustrates an example that shows crossover for two chromosomes. In this non-limiting example, parent chromosomes 404, 408 recombine via crossover to form offspring chromosomes 412, 416. Each of the chromosomes 404-416 has four genes, although a different number of genes can be used in other examples. In the illustrated example of crossover, as shown by arrow 420, the first gene 420a from the parent chromosome 404 is crossed over to become the first gene 420b of the offspring chromosome 416, and as shown by arrow 424, the first gene 424a from the parent chromosome 408 is crossed over to become the first gene 424b of the offspring chromosome 412.

FIG. 4 shows one illustrative, non-limiting example of a one-point crossover technique. In other embodiments, the crossover point on the chromosomes may be different from the first gene. For example, the position of the cross-over point in a chromosome may be selected randomly. In other embodiments, two-point (or multiple-point) cross-over techniques can be used. In other embodiments, "cut and slice" approaches in which the crossover point is different for each chromosome can be used. Such approaches lead to changes in the lengths of offspring chromosomes. In other embodiments, probabilistic crossover techniques can be used such as, e.g., uniform or half-uniform crossover approaches. Many crossover approaches may be used in various embodiments of the systems and methods described herein.

II. Examples of Mutation

In the example method 300, mutation at block 340 is used to maintain or increase genetic diversity from one generation of chromosomes to the next generation. In the example method 300, mutation at block 340 is performed after crossover at block 336. In other embodiments, mutation can be performed before crossover or mutation and crossover can be performed together as part of a chromosomal breeding operation.

In one possible implementation of a mutation operator, a mutation probability, $Pm \leq 1$, is used. The mutation probability may be predefined, set by a user, and/or be an adjustable parameter that changes during the evolution. In some embodiments of mutation, an arbitrary bit in a gene in a chromosome is changed (e.g., flipped) from its original state with probability Pm. In other embodiments of mutation, a gene in a chromosome is replaced by a gene from the gene pool. In some of these embodiments, the mutation probability Pm is set at a relatively higher value than that used in certain mutation algorithms using bit-flipping. A relatively higher mutation probability can allow more genes from the gene pool to have a chance to participate in the selection process. Mutation can be applied to one, two, three, four, or more of the genes in a chromosome. In some implementations, the evolution starts with a value of Pm=0.5. In some such implementations, the index selection subsystem may increase the value of the mutation probability if little or no fitness improvement is found after a number of generations.

In some embodiments of mutation, gene selection from the gene pool may satisfy one or more of the following criteria.

1. Gene selection is based at least in part on the participation probability for the genes in the gene pool.
2. A gene selected from the gene pool is not same as the gene that is going to be mutated.
3. A gene selected from the gene pool does not exist in the chromosome that is going to be mutated.
4. If a composite index candidate is selected from the gene pool, an embodiment of the composite index construction method described above can be used to construct a composite index gene for mutation.

Figure 5:
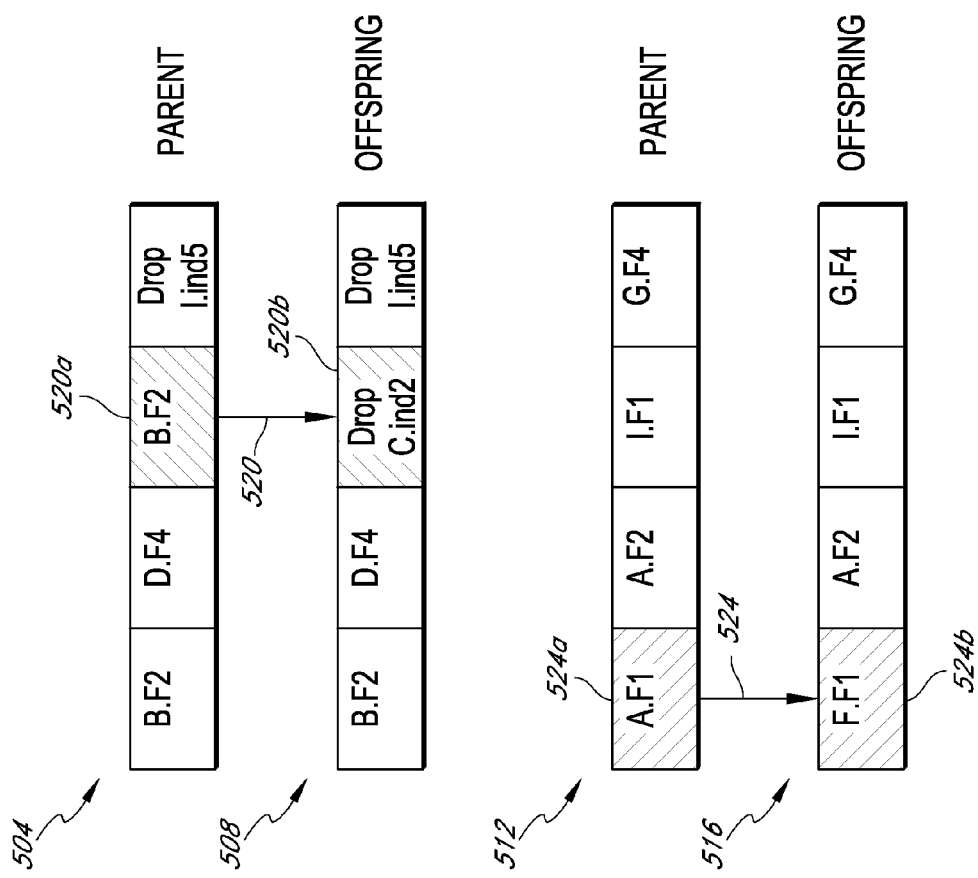
FIG. 5 illustrates two examples of gene mutation.

FIG. 5 illustrates two non-limiting examples of gene mutation. In example (A), as shown by arrow 520, gene 520a in parent chromosome 504 mutates into gene 520b in offspring chromosome 508. In example (B), as shown by arrow 524, gene 524a in parent chromosome 512 mutates into gene 524b in offspring chromosome 516. In other example, the chromosomes may have different lengths than shown, and a different number or location of genes can mutate.

In the example method 300 illustrated in FIGS. 3A-3B, after chromosomal breeding at block 336 for crossover and at block 340 for mutation transforms the population of chromosomes into an offspring population, at block 344 the offspring chromosomes are placed in an offspring pool, which is prepared for the next generation of evolution. In some embodiments, at least some of the parent chromosomes may also be placed in the offspring pool (e.g., to provide elitism).

In some implementations, the desired number of chromosomes in the offspring pool is denoted by N. The value of N can be predefined, set by a user, and/or adjustable during evolution. At block 348 of the example illustrated in FIGS. 3A-3B, the method 300 determines whether the offspring pool size is equal to N. If not, the method 300 can return to block 336 (and then block 340) to generate additional offspring. In some implementations, some of the parent chromosomes are included in the offspring pool to provide for elitism. If the offspring pool size is equal to N, then the crossover and mutation operations at blocks 336 and 340 (or other suitable genetic operations) have generated an offspring pool having the desired population size N.

Continuing with the example method 300, after the offspring pool has been generated, at block 352, the current chromosome population in the population pool is replaced by the chromosomes in the offspring pool. In some embodiments, only some of the offspring chromosomes are moved to the population pool. The example method 300 returns to block 320 to start the next generation of evolution.

If the termination criterion or criteria at block 332 indicate that the evolution should terminate, at block 356, the example method 300 returns or stores the best (e.g., most fit) chromosome (or several chromosomes with the highest fitness), which represents the best (e.g., least costly) index configuration(s) for the database. Other information related to the evolution may also be returned or stored in a computer-readable medium.

Although FIGS. 2 and 3 illustrate examples of methods that can be used to solve the Index Selection problem for one or more databases, these examples are intended to illustrate and not to limit the scope of the disclosure set forth herein.

CONCLUSION

Thus embodiments of the foregoing systems and methods can be used to find an index configuration for a collection of data such as, e.g., a database. In some applications, evolution over about 100 generations for a database having about 20 tables with about 50 SQL statements can find an index configuration that has a performance (e.g., measured by cost) comparable to an index configuration that can be found using human knowledge to search the search space.

When the database is modified or updated (e.g., new tables are added to the database), an updated index configuration may be found using such embodiments. In some implementations, rather than starting the Gen(0) population from a random initial population, the last one or last few generations of chromosomes that were used to find the previous index configuration may be used to restart the evolution. Therefore, such implementations can advantageously learn from prior evolution and may be able to find an updated index configuration more efficiently than starting from a random Gen(0) population.

Embodiments of the systems and methods described herein can be used for applications other than the Index Selection problem. For example, in other embodiments, the systems and methods can be used for other database configuration recommendations such as determining materialized views and/or table partitions for a target database. In other implementations, embodiments of the systems and methods may be used to search a search space for a solution to a combinatorial optimization problem such as, e.g., a routing problem, a constraint satisfaction problem, and so forth.

In certain embodiments, the systems and methods described herein can advantageously be implemented, fully or in part, using computer software, hardware, firmware, or any combination of software, hardware, and firmware. In one embodiment, the system is implemented as a number of software modules that comprise computer executable code for performing the functions described herein. In certain embodiments, the computer-executable code is executed on one or more general purpose computers. However, a skilled artisan will appreciate, in light of this disclosure, that any module that can be implemented using software to be executed on a general purpose computer can also be implemented using a different combination of hardware, software or firmware. For example, such a module can be implemented completely in hardware using a combination of integrated circuits. Alternatively or additionally, such a module can be implemented completely or partially using specialized computers designed to perform the particular functions described herein rather than by general purpose computers.

Further, certain embodiments of the invention are described with reference to methods, apparatus (e.g., systems) and computer program products that can be implemented by computer program instructions. These computer program instructions can be provided to a processor of a general purpose computer, special purpose computer, or other programmable data processing apparatus to produce a machine, such that the instructions, which execute via the processor of the computer or other programmable data processing apparatus, create means for implementing the acts specified herein to transform data from a first state to a second state.

Computer program instructions can be stored in a computer-readable storage medium or memory that can direct a computer or other programmable data processing apparatus to operate in a particular manner, such that the instructions stored in the computer-readable storage medium produce an article of manufacture including instruction means which implement the acts specified herein. The computer-readable storage medium or memory may include a non-transitory computer-readable storage medium such as, e.g., magnetic, semiconductor, or optical storage.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the acts specified herein.

Depending on the embodiment, certain acts, events, blocks, modules, or functions of any of the methods, algorithms, or systems described herein can be performed in a different sequence, may be added, merged, rearranged, or left out all together. Thus, in certain embodiments, not all described acts, events, blocks, modules, or functions are necessary for the practice of the methods, algorithms, or systems. Moreover, in certain embodiments, acts, events, blocks, modules, or functions may be performed concurrently, e.g., through multi-threaded processing, parallel processing, interrupt processing, or via multiple processors or processor cores, rather than sequentially.

Conditional language such as, among others, "can," "could," "might" or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While certain embodiments of the inventions have been described, these embodiments have been presented by way of example only, and are not intended to limit the scope of the disclosure. Indeed, the novel methods and systems described herein may be embodied in a variety of other forms; furthermore, various omissions, substitutions and changes in the form of the methods and systems described herein may be made without departing from the spirit of the disclosure. Thus, nothing in the foregoing description is intended to imply that any particular feature, characteristic, step, module, or block is necessary or indispensable to each embodiment. The accompanying claims and their equivalents are intended to cover such forms or modifications as would fall within the scope and spirit of the disclosure.

What is claimed is:

1. A method for finding an index configuration for a database, the method comprising:
   under control of a computing system comprising one or more physical computing devices,
   determining, from a plurality of structured query language (SQL) statements for a database, a set of index candidates for the database, the index candidates comprising at least one of: (1) a column in a table in the database, (2) disabling an index associated with a table in the database, and (3) a composite index for the database, the composite index comprising a plurality of columns from at least one table in the database;
   forming a gene pool comprising a plurality of genes associated with the index candidates for the database, wherein each gene in the gene pool is a representation of an index candidate from the set of index candidates, the representation comprising an alphanumeric identifier for the index candidate;
   determining a participation probability for each gene in the gene pool, the participation probability for a gene based at least in part on a total cost of the plurality of SQL statements for the index candidate associated with the gene;
   generating a parent population of chromosomes, each chromosome comprising one or more genes from the gene pool, wherein the generating comprises filling a gene in a chromosome based at least in part on the participation probability for that gene;
   evolving the parent population of chromosomes to form an offspring population of chromosomes, wherein the evolving comprises applying at least one of a crossover operator and a mutation operator to at least some of the chromosomes in the parent population;
   determining a fitness of each of the chromosomes in the offspring population;
   evaluating whether to terminate the evolving based at least in part on a termination criterion; and
   providing information associated with one or more of the chromosomes in the offspring population.

2. The method of claim 1, wherein the database comprises a relational database.

3. The method of claim 1, wherein the alphanumeric identifier comprises alphanumeric information identifying a table of the database and a column of the table.

4. A system for managing index configurations for a database, the system comprising:
   an index selection subsystem configured to communicate with a data repository configured to store a database, the index selection subsystem configured to execute one or more modules on a computing device, the index selection subsystem comprising:
   a population module configured to provide a population of chromosomes that represent possible index configurations for the database, wherein a chromosome comprises at least one gene associated with a possible index candidate for the database;
   wherein the population module is configured to provide the population of chromosomes by selecting genes for the chromosomes based at least in part on a participation probability for the gene, the participation probability based at least in part on a cost of SQL statements for the index candidate associated with the gene;
   a fitness module configured to provide a fitness for each of the chromosomes in the population;
   an evolution module configured to evolve the population of chromosomes based at least in part on one or more genetic operators, the evolution module further configured to (1) increase the number of chromosomes in the population in response to a first criterion or (2) increase the length of at least some of the chromosomes in the population in response to a second criterion; and
   an interface module configured to provide information associated with one or more of the chromosomes in the population.

5. The system of claim 4, wherein the population module is configured to represent an index candidate in a gene based at least in part on an alphanumeric identifier for the index candidate.

6. The system of claim 4, wherein the population module is configured to provide the population of chromosomes by retrieving from the data repository information related to a prior evolution of chromosomes for the database.

7. The system of claim 4, wherein the fitness module is configured to provide the fitness of a chromosome based at least in part on a cost of a plurality of structured query language (SQL) statements for an index configuration comprising the index candidates associated with the genes in the chromosome.

8. The system of claim 4, wherein the evolution module is further configured to terminate the evolution of the population based on one or more termination criteria, the termination criteria comprising one or more of: (1) a number of generations of the population, (2) an elapsed time, (3) a time-of-day, (4) an amount of computer processing time, (5) an amount of computer resources used by the system, and (6) a threshold level of fitness.

9. The system of claim 8, wherein the interface module is configured to provide information associated with the chromosome having the greatest fitness in the population when the evolution is terminated.

10. The system of claim 4, wherein the first criterion comprises determining whether increasing the length of at least some of the chromosomes in a prior population led to a significant fitness improvement after a threshold number of generations of evolution.

11. The system of claim 4, wherein the second criterion comprises determining whether increasing the number of chromosomes in a prior population led to a significant fitness improvement after a threshold number of generations of evolution.

12. The system of claim 4, wherein the database comprises a plurality of tables, each of the tables comprising one or more columns of data, and the index candidates comprise (1) a column in one of the plurality of tables in the database, (2) disabling an index from one of the plurality of tables in the database, and (3) a composite index for the database, the composite index comprising a plurality of columns from one or more of the plurality of tables in the database.

13. The system of claim 12, wherein, for an index candidate comprising a composite index for the database, the population module is configured to determine a length for the composite index based at least in part on a probability distribution for lengths of composite index candidates.

14. The system of claim 13, wherein the population module is further configured to select columns for the composite index based at least in part on a participation probability for the column.

15. A method for recommending an index configuration for a collection of data, the method comprising:
 analyzing a plurality of transactions for a collection of data to determine a set of index candidates for the collection of data;
 generating a group of index configurations for the collection of data, each index configuration associated with a plurality of index candidates from the set of index candidates, the index candidates represented in the index configuration as a non-bitmapped data structure;
 evaluating a fitness of each index configuration in the group of index configurations, the fitness based at least in part on a change in computer resources associated with using the index configuration when executing the plurality of transactions on the collection of data;
 for each index configuration in the group of index configurations, changing a first index candidate of the plurality of index candidates in the index configuration, wherein changing the first index candidate comprises:
  replacing the first index candidate with a second index candidate selected from the set of index candidates based at least in part on a mutation probability, the second index candidate different from the first index candidate; or
  replacing the first index candidate with a second index candidate selected from a second index configuration from the group of index configurations, the second index configuration selected based at least in part on a recombination probability, the recombination probability based at least in part on the fitness associated with the second index configuration;
 modifying the group of index configurations by (1) adding new index configurations to the group of index configurations, the new index configurations comprising index candidates selected from the set of index candidates, (2) adding new index candidates from the set of index candidates to each of the index configurations present in the group of index configurations, or both (1) and (2);
 repeating, one or more times, evaluating the fitness, changing the first index candidate, and modifying the group of index configurations; and
 recommending, from the group of index configurations, the index configuration having the greatest fitness,
 wherein the method is performed by a computing system comprising one or more physical computing devices.

16. The method of claim 15, wherein the collection of data comprises a database.

17. The method of claim 16, wherein the transaction comprises a structured query language (SQL) transaction on the database.

18. The method of claim 15, wherein the non-bitmapped data structure comprises alphanumeric characters.

19. The method of claim 15, wherein generating the group of index configurations for the collection of data comprises:
 determining, for each of the index candidates in the set of index candidates, a change in the computer resources associated with using an index comprising the index candidate when executing the plurality of transactions on the collection of data;
 determining, for each index candidate in the set of index candidates, a participation probability based at least in part on the change in the computer resources associated with the index candidate; and
 selecting, for each index configuration in the group of index configurations, index candidates based at least in part on the participation probability associated with the index candidate.

* * * * *